United States Patent [19]

Goldhaft et al.

[11] 4,022,911

[45] May 10, 1977

[54] DISINFECTANT COMPOSITION COMPRISING A QUATERNARY AMMONIUM COMPOUND, A PHENOL, AND FORMALDEHYDE

[75] Inventors: Tevis M. Goldhaft; Charles Kaitz, both of Vineland; George D. Maier, Bridgeton, all of N.J.

[73] Assignee: Damon Corporation, Needham Heights, Mass.

[22] Filed: May 29, 1975

[21] Appl. No.: 581,728

Related U.S. Application Data

[63] Continuation of Ser. No. 287,770, Sept. 11, 1972, abandoned, which is a continuation-in-part of Ser. No. 94,538, Dec. 2, 1970, abandoned, which is a continuation-in-part of Ser. No. 663,552, Aug. 28, 1967, abandoned.

[52] U.S. Cl. .............................. 424/329; 424/324; 424/330; 424/331; 424/334; 424/340; 424/342; 424/346; 424/347; 424/348

[51] Int. Cl.² .................. A01N 9/02; A01N 9/20; A01N 9/24; A01N 9/26

[58] Field of Search ........... 424/329, 334, 346, 342

[56] References Cited

UNITED STATES PATENTS

| | | | |
|---|---|---|---|
| 2,347,012 | 4/1944 | Waugh | 424/226 |
| 2,702,774 | 2/1955 | Stayner | 424/329 |
| 2,793,976 | 5/1957 | McKinney | 424/78 |
| 2,998,390 | 8/1961 | Hamilton | 424/76 |
| 3,287,214 | 11/1966 | Taylor et al. | 424/45 |

OTHER PUBLICATIONS

McCutcheon's Detergents & Emulsifiers, 1967 Annual, p. 154, received June 19, 1967.

*Primary Examiner*—Allen J. Robinson
*Attorney, Agent, or Firm*—Kenway & Jenney

[57] ABSTRACT

A disinfectant composition is made with three essential active ingredients comprising (1) a quaternary ammonium compound, (2) a phenol or a derivative thereof, and (3) formaldehyde. The composition provides enhanced disinfecting efficacy of a synergistic nature, since the composition is more inhibitory and/or lethal to a greater variety of bacteria than is any one of its components or the sum of the separate effects of its components.

4 Claims, No Drawings

DISINFECTANT COMPOSITION COMPRISING A QUATERNARY AMMONIUM COMPOUND, A PHENOL, AND FORMALDEHYDE

This application is a continuation of our application Ser. No. 287,770 filed Sept. 11, 1972, now abandoned, which was a continuation-in-part of our application Ser. No. 94,538, filed Dec. 2, 1970, now abandoned which in turn was a continuation-in-part of our application Ser. No. 663,552, filed Aug. 28, 1967, and now abandoned.

This invention relates to a disinfectant composition having particular utility and value when used in poultry and animal husbandry, but also having broader applications as well.

The use of disinfectants in poultry and animal husbandry is virtually essential for carrying on profitable operations. In this industry there are several important yardsticks by which the value of any particular disinfectant is generally assessed. One of these is the range of virulent micro-organisms against which the disinfectant is effective. This is important because the greater the range of effectiveness, the more versatile and reliable is the disinfectant for destroying the multitude of harmful microorganism species which are commonly encountered in poultry and animal husbandry. Another important consideration is the capability of the disinfectant to remain effective as its use level concentration is decreased. This is largely an economic consideration but nevertheless highly important, since the less of the disinfectant that can be effectively used, the lower will be the cost of carrying out the disinfecting process.

The present invention provides a new disinfectant composition which has unprecedented value in poultry and animal husbandry when measured by the yardsticks described above. First of all, the composition has an exceptionally broad range of effectiveness against many different species of virulent microorganisms, including bacteria, fungi, viruses, worm eggs and coccidial oocysts. More specifically, the disinfectant composition of the invention has been demonstrated to effectively destroy Salmonella group, Pasteurella group, Brucella group, Staphylococci, Streptococci, Erysipelothrix rhusiopathiae, Micrococci, Listerella group, Arizona paracolon, Escherichia coli, Vibrio group, Aspergillus sp., Penicillin sp., Monilia sp., Coccidial oocysts, Ascaridia galli eggs, Newcastle disease virus, Infectious bronchitis, Fowl pox, Laryngotracheitis, Avian encephalitis and Leukosis. Thus, the versatility of the new disinfectant composition is very great, whereby the composition may be used as a single substitute for two or more conventional disinfectants that have been heretofore necessary to combat more than one of the above-specified microorganisms.

In addition to its broad range of effectiveness, the new disinfectant composition has greater destructive power than does any one of its components or the sum of the separate effects of its components. In other words, the components of the composition interact synergistically, in some unexplainable manner, to give a disinfecting effect beyond that would be expected by measuring the separate effect of each component and adding the results up. This attribute of the composition has been demonstrated by laboratory tests with several of the microorganism species named above and was entirely surprising and unexpected. Furthermore, the synergistically superior disinfecting capability of the composition means that it may be effectively used at very high dilutions, or conversely low levels of concentration, to provide substantial cost-of-material savings to the user. This advantage combined with its versatility makes the composition extremely valuable as an all-around, general purpose disinfectant for use in poultry and animal husbandry. However, the composition may also be used to advantage in other applications, such as in hospitals, kitchens, comfort stations, laboratories, and other locations which have hygienic requirements.

As previously mentioned, the disinfectant composition of the invention contains three essential active ingredients, viz., a dimethyl quaternary ammonium halogen salt; a phenol or a derivative thereof; and formaldehyde.

The first ingredient is a dimethyl quaternary ammonium halogen salt and is represented by the following formula:

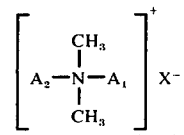

wherein:

X is bromine, chlorine or iodine, $A_1$ is an alkyl, alkoxy, aryl or aroyl radical, and $A_2$ is an alkyl, alkoxy, aryl or aroyl radical.

It will be understood that there could be combined water in many of the compounds and that the above formula includes these compounds with combined water.

Suitable dimethyl quaternary ammonium halogen salts include benzalkonium and benzethonium halides, alkylbenzyldimethylammonium halides, alkyldimethyl(dimethylbenzyl) ammonium halides, benzyldimethylphenylammonium halides, dialkyldimethylammonium halides, alkyltrimethylammonium halides, alkylbenzyltrimethonium halides and xylylene analogs thereof. Benzalkonium halide is alkyl dimethyl benzyl ammonium halide in which the alkyl group varies from eight to eighteen carbon atoms, and benzethonium halide is diisobutylphenoxyethoxyethyl dimethyl benzyl ammonium halide. Both of these materials are available commercially, usually as the chloride, under various tradenames such as Zephirol, BTC, Roccal, Phemeride, Quatrachlor, Solamine and others. Any of these commercially available benzalkonium or benzethonium chloride salts, as well as the bromide and iodide salts, may be used as one of the essential ingredients of the disinfectant composition of the invention. A typical alkylbenzyltrimethonium halide is methyl dodecylbenzyl trimethyl ammonium chloride having the following structural formula:

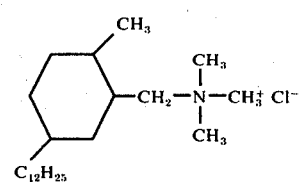

An example of a xylylene analog of an alkylbenzyltrimethonium halide is methyl dodecylxylylene bis (trimethyl ammonium chloride) which has the following structural formula:

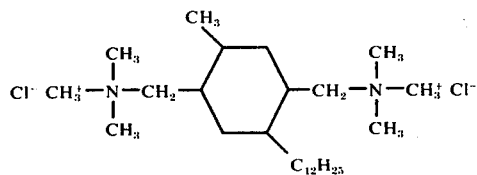

Good results have been obtained with a mixture of these compounds, which is commercially available from Rohm & Haas under the tradename Hyamine 2389. Of all the quaternary ammonium salts, best results have been obtained with benzalkonium chloride and benzethonium chloride.

The second ingredient of the composition is a phenol or a substituted derivative thereof. The derivative may contain one or more aryl aliphatic or halogen radicals. The second ingredient is represented by the following formula:

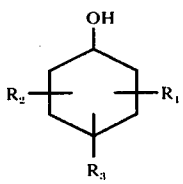

wherein:
$R_1$ is hydrogen, a halogen, a nitro group, an amino group, an alkyl, alkoxy, aryl or aroyl group having no more than about seven carbon atoms, $R_2$ is hydrogen, a halogen, a nitro group, an amino group, an alkyl, alkoxy, aryl or aroyl group having no more than about seven carbon atoms, and $R_3$ is hydrogen, a halogen, a nitro group, an amino group, an alkyl, alkoxy, aryl or aroyl group having no more than about seven carbon atoms.

In the preferred embodiment, the second ingredient of the composition is a phenol or a halogen and/or hydrocarbon substituted derivative thereof wherein there are no more than two substitutions on the benzene ring and wherein the hydrocarbon has from one to seven carbon atoms. This embodiment of the second ingredient is represented by the following formula:

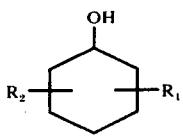

wherein:
$R_1$ is hydrogen or a halogen or an alkyl group having from 1 to about 7 carbon atoms, and $R_2$ is hydrogen or a halogen or an alkyl group having from 1 to about 7 carbon atoms.

Excellent results have been obtained with a cresol or an alkyl derivative thereof having from one to seven carbon atoms. The composition is defined by the following formula:

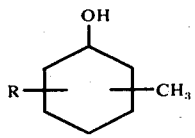

in which R is hydrogen atom or a branched or straight chain alkyl group having from one to seven carbon atoms. Of the various compounds defined by the above formula, best results have been achieved with 2-isopropyl-5-methyl-phenol in combination with benzalkonium halide and para-cresol in combination with benzethonium halide. Accordingly, the use of these particular compounds is recommended for the maximum benefits in terms of range and power of disinfecting effectiveness.

As to the third ingredient of the composition, which is formaldehyde, this may be used in the form of the commercially available aqueous solutions (Formalin) or in the solid form, paraformaldehyde, usually depending on whether the composition is made as a liquid or solid product.

In preparing the novel disinfecting composition of the invention, the best results have been achieved when the three essential ingredients are controlled within the relative proportions expressed in parts by weight of about 1 to about 20 parts of the quaternary ammonium salt, about 1 to about 20 parts of the phenol or derivative thereof and about 10 to about 150 parts of formaldehyde. In particular, the synergistic quality of the disinfectant composition will invariably be achieved when the proportions of the three essential ingredients are maintained within the stated ranges. Therefore, for best results, it is again recommended that the composition be made according to these relative proportions.

Where the composition is to be made as a liquid product, the three essential ingredients may be conveniently dissolved in water or in water with admixed low molecular weight alcohols such as methanol and ethanol. It is also convenient to make the liquid product in the form of a concentrated solution in which the total amount of the three essential ingredients constitutes from about 6 to about 50% of the weight of the solution. This concentrated solution may be packaged and shipped at relatively low cost and then diluted by the addition of water by the user to whatever lower concentration is necessary to carry out the desired disinfecting process.

The disinfecting composition may also be made in the form of a solid product by using paraformaldehyde and those of the cresol compounds which are solid at ambient temperature, e.g., para-cresol. In preparing a solid product it is highly desirable to include inorganic salts which will help to solubilize the paraformaldehyde and solid cresol compound when the solid product is combined with water for actual use. In this connection, excellent results have been achieved with trisodium phosphate as an added inorganic salt which assists solubilization. However, other salts may also be used including mono and dihydrogen sodium phosphates, sodium bisulfate, sodium bicarbonate, sodium carbonate and sodium pyrophosphate.

In preparing a solid product, the total amount of the three essential ingredients may constitute from about 6 to about 65% of the weight of the total product, the balance being one or more of the inorganic salts mentioned above. The solid product may be dissolved in water or water plus the previously-mentioned organic alcohols at whatever concentration is necessary for carrying out the desired disinfecting process. In both the liquid and solid product, the relative proportions of the three essential ingredients should be controlled for best results with the ranges previously specified, in both the prepared form and in the diluted form of actual use. Of course, if the prepared product is controlled within the specified relative proportions, then those same proportions will be maintained no matter how much the prepared product is diluted for actual use.

Further details of the invention will be readily understood in connection with the following examples which constitute specific embodiments thereof and in which all proportions are expressed on the basis of weight unless otherwise indicated.

EXAMPLE I

A disinfectant composition was made by admixing benzalkonium chloride, 2-isopropyl-5-methyl-phenol and formaldehyde in the relative proportions of 2 parts benzalkonium chloride, 2.5 parts of 2-isopropyl-5-methyl-phenol and 25 parts of formaldehyde solution (37% formaldehyde, 12% methanol, 51% water). The composition was dissolved in 70.5 parts of a mixture of ethyl alcohol and methyl alcohol in the proportion of 1 part of methyl alcohol to 3 parts of ethyl alcohol to give a concentrated solution which when diluted with water in the ratio of 1:100 gave a solution having 200 ppm of the benzalkonium chloride, 250 ppm of the 2-isopropyl-5-methyl-phenol and 2500 ppm of the formaldehyde. The efficacy of the composition at this dilution level and at further dilutions in the ratios of 1:1000, 1:2000, 1:4000, 1:8000, and 1,16000, to inhibit the growth of and to kill Staphylococcus aureaus was measured according to the standard laboratory test described by Kolmer and Boerner in Approved Laboratory Technic, Fourth Edition, published by D. Appleton-Century Company, Incorporated. Likewise, each of the separate components of the composition, at the same dilutions and by the same test, was separately tested to measure the efficacy of each component alone to arrest the growth of and to kill the same specie of bacteria.

The results of these tests are given in the table below, the column labeled Inhibitory giving the maximum dilution at which the material under test could arrest the growth of the bacteria and the column labeled Lethal giving the maximum dilutions at which the material under test could kill the bacteria.

| Material Tested | Staphylococcus aureaus | |
| --- | --- | --- |
| | Inhibitory | Lethal |
| Benzalkonium chloride alone | 1:2000 | 1:1000 |
| 2-isopropyl-5-methyl-phenol alone | 1:1000 | 1:1000 |
| Formaldehyde alone | 1:4000 | 1:4000 |
| Above three combined | 1:16000 | 1:16000 |

As will be noted from the foregoing results, the combination of the three essential ingredients in accordance with the present invention was more inhibitory and more lethal to the bacteria than was any one of the components alone or the sum of the separate effects of each component. Thus, normally one would expect that the combination of the three ingredients would give an effect approximately equal to the algebraic sum of the separate effects measured in the test. However, this was not the case and the effect of the combination of the ingredients exceeded the best performance given by the best component alone. Thus, the disinfectant composition of three essential ingredients made according to the invention was surprisingly and unexpectedly superior, and this result could not be explained except for synergism.

EXAMPLE 2

Example 1 was repeated with a specie of fungi, Candida albicans, and the measured results are given in the table below:

| Material Tested | Candida albicans | |
| --- | --- | --- |
| | Inhibitory | Lethal |
| Benzalkonium chloride alone | 1:100 | 1:100 |
| 2-isopropyl-5-methyl-phenol alone | 1:100 | 1:100 |
| Formaldehyde alone | 1:100 | 1:100 |
| Above three combined | 1:4000 | 1:1000 |

As will be noted, the combination of the three essential ingredients made in accordance with the invention was again more inhibitory and more lethal than was the best of its separate components. Again, this result could not be explained except for synergism.

EXAMPLE 3

Example 1 was again repeated with another specie of fungi, Aspergillus fumigatus, and the measured results are given in the table below:

| Material Tested | Aspergillus fumigatus | |
| --- | --- | --- |
| | Inhibitory | Lethal |
| Benzalkonium chloride alone | — | — |
| 2-isopropyl-5-methyl-phenol alone | 1:1000 | — |
| Formaldehyde alone | 1:2000 | 1:2000 |
| Above three combined | 1:8000 | 1:2000 |

As will be noted, with this specie of fungi, the combination of the three ingredients was more inhibitory and equally as lethal as the best of its separate components alone. Thus, once again in the combination of the three ingredients was more effective as a disinfectant because of synergistic interaction between the ingredients in the combination.

EXAMPLE 4

A solid disinfectant composition was made in accordance with the invention by combining 20 parts of benzethonium chloride, 25 parts of para-cresol and 275 parts of paraformaldehyde as the essential active ingredients, and 180 parts of a trisodium phosphate were included as a solubilization aid.

This 500 gram quality of the composition, when dissolved in 100 liters of water, provided concentrations of the three essential ingredients equivalent to the concentrations of the 1:100 dilution specified in Examples 1–3 above. The dissolved product was an extremely effective disinfectant against many of the microorganism species mentioned at the beginning of this specification, to a degree equivalent to the synergistic superiority exhibited in the tests of Examples 1–3.

EXAMPLE 4A

Example 4 was repeated except that no solubilization aid was employed. The combination was considerably more difficult to dissolve than the combination with the solubilization aid.

When the product was finally dissolved at the 1:100 dilution specified in Examples 1–3, the product was found to act synergistically to the same degree as the composition of Example 4.

EXAMPLE 5

A disinfectant composition was made by admixing 2 g. benzalkonium chloride (50%), 1 g. 2-isopropyl-5-methyl-phenol, and 400 g. formaldehyde (37%) which may be stated in relative proportions as 1 part benzalkonium chloride, 1 part 2-isopropyl-5-methyl-phenyl and 150 parts of formaldehyde. The composition was placed in a 500 ml. volumetric flask and diluted with a quantum sufficit of denatured ethanol. The dissolved mixture was then diluted with water to yield a composition having 10 ppm benzalkonium chloride, 10 ppm 2-isopropyl-5-methyl-phenol and 1500 ppm formaldehyde. In like manner, each of the separate components of the composition was prepared, but at double the strength of the combination of ingredients. 1 cc. of each solution was pipetted into a screw cap tube. To each tube was added 1 cc. of 24 hour broth culture of salmonella pullorum adjusted to a $10^{-3}$ of 1 × MacFarland No. 1 with sterile saline. Each tube was left standing at room temperature for 5 minutes and then 0.1 ml. of the mixture was admixed with 9.9 ml. of tryptose broth. 0.1 ml. of this mixture in the tryptose broth tube was transferred to a plate with a brainheart infusion agar and the plate was incubated at 37° C. for 4 days. Each plate was then analyzed to determine whether or not growth of bacteria was inhibited. The results of the test are as follows:

| Material Tested | Dilution | Growth Inhibited |
|---|---|---|
| Benzalkonium chloride | 20 ppm. | No |
| 2-isopropyl-5-methyl-phenol | 20 ppm. | No |
| Formaldehyde | 3000 ppm. | No |
| Above 3 combined at one-half strength | | |
| Benzalkonium chloride | 10 ppm. | |
| 2-isopropyl-5-methyl-phenol | 10 ppm. | Yes |
| Formaldehyde | 1500 ppm. | |

As can be seen from the chart above none of the individual components inhibited growth but yet the combination of the 3 ingredients acted synergistically and inhibited growth of the salmonella pullorum even though it was at one half the strength of each of the materials tested alone. This is completely unexpected and surprising and cannot be explained except for the synergism of the 3 ingredients when used in combination.

EXAMPLE 6

The test of Example 5 was repeated with a disinfectant composition comprising in relative proportions 20 parts benzalkonium chloride, 1 part 2-isopropyl-5-methyl-phenol and 150 parts formaldehyde. The results of the test are given in the chart below.

| Material Tested | Dilution | Growth Inhibited |
|---|---|---|
| Benzalkonium chloride | 400 ppm. | No |
| 2-isopropyl-5-methyl-phenol | 20 ppm. | No |
| Formaldehyde | 3000 ppm. | No |
| Above 3 combined at one-half strength | | |
| Benzalkonium chloride | 200 ppm. | |
| 2-isopropyl-5-methyl-phenol | 10 ppm. | Yes |
| Formaldehyde | 1500 ppm. | |

Again none of the ingredients was sufficient by itself to inhibit growth but yet the combination of the 3 ingredients inhibited growth even though it was used at one half the strength of the individual ingredients and this surprising result must be attributed to synergism.

EXAMPLE 7

The test of Example 5 was repeated with the disinfectant composition comprising in relative proportions 1 part benzalkonium chloride, 20 parts 2-isopropyl-5-methyl-phenol and 150 parts formaldehyde. The results of the test are given in the chart below.

| Material Tested | Dilution | Growth Inhibited |
|---|---|---|
| Benzalkonium chloride | 20 ppm. | No |
| 2-isopropyl-5-methyl-phenol | 400 ppm. | No |
| Formaldehyde | 3000 ppm. | No |
| Above 3 combined at one half strength | | |
| Benzalkonium chloride | 10 ppm. | |
| 2-isopropyl-5-methyl-phenol | 200 ppm. | Yes |
| Formaldehyde | 1500 ppm. | |

As in the previous examples the individual ingredients would not inhibit growth but yet the synergistically acting combination of all 3 ingredients inhibited growth even though it was used at one half the strength of the individual ingredients.

EXAMPLE 8

The testing procedure of Example 5 was used on a disinfectant composition comprising in relative proportions 20 parts benzalkonium chloride, 20 parts 2-isopropyl-5-methyl-phenol and 20 parts formaldehyde. The results of these tests are summarized in the chart below.

| Material Tested | Dilution | Growth Inhibited |
|---|---|---|
| Benzalkonium chloride | 400 ppm. | No |
| 2-isopropyl-5-methyl-phenol | 400 ppm. | No |
| Formaldehyde | 200 ppm. | No |
| Above 3 combined at one half strength | | |
| Benzalkonium chloride | 200 ppm. | |
| 2-isopropyl-5-methyl-phenol | 200 ppm. | Yes |
| Formaldehyde | 100 ppm. | |

Once again the combination of ingredients work synergistically to inhibit growth whereas none of the individual ingredients inhibited growth even through the individual ingredients were used as twice the strength of the combination of ingredients.

EXAMPLE 9

The test of Example 5 was repeated on a disinfectant composition having in relative proportions 1 part benzalkonium chloride, 20 parts 2-isopropyl-5-methyl-phenol and 10 parts formaldehyde. The results of these tests are as follows:

| Material Tested | Dilution | Growth Inhibited |
|---|---|---|
| Benzalkonium chloride | 20 ppm. | No |
| 2-isopropyl-5-methyl-phenol | 400 ppm. | No |
| Formaldehyde | 200 ppm. | No |
| Above 3 combined at one half strength | | |
| Benzalkonium chloride | 10 ppm. | |
| 2-isopropyl-5-methyl-phenol | 200 ppm. | Yes |
| Formaldehyde | 100 ppm. | |

The synergistically acting combination of the 3 ingredients at one half the strength of the individual ingredients gave the surprising result of inhibiting growth whereas the individual ingredients would not inhibit the growth and this inhibition of growth by the combination can only be explained by the 3 ingredients working synergistically together.

EXAMPLE 10

Example 5 was repeated with a disinfectant composition comprising in relative proportions 20 parts benzalkonium chloride, 1 part 2-isopropyl-5-methyl-phenol and 10 parts formaldehyde. The test results are given below:

| Material Tested | Dilution | Growth Inhibited |
|---|---|---|
| Benzalkonium chloride | 400 ppm. | No |
| 2-isopropyl-5-methyl-phenol | 20 ppm. | No |
| Formaldehyde | 200 ppm. | No |
| Above 3 combined at one half strength | | |
| Benzalkonium chloride | 200 ppm. | |
| 2-isopropyl-5-methyl-phenol | 10 ppm. | Yes |
| Formaldehyde | 100 ppm. | |

As in previous examples the combination of ingredients acted synergistically to inhibit growth whereas the individual ingredients even at twice the strength of the combination would not inhibit growth.

EXAMPLE 11

The test of Example 5 was repeated with a disinfectant composition comprising 1 part benzalkonium chloride, 1¼ parts 2-isopropyl-5-methyl-phenol and 12½ parts formaldehyde. The results of the test are given below.

| Material Tested | Dilution | Growth Inhibited |
|---|---|---|
| Benzalkonium chloride | 200 ppm. | No |
| 2-isopropyl-5-methyl-phenol | 250 ppm. | No |
| Formaldehyde | 2500 ppm. | No |
| Above 3 combined at one half strength | | |
| Benzalkonium chloride | 100 ppm. | |
| 2-isopropyl-5-methyl-phenol | 125 ppm. | Yes |
| Formaldehyde | 1250 ppm. | |

As can be seen from the chart the individual ingredients did not inhibit growth of the bacteria but yet the synergistically acting combination of the 3 ingredients at one half the strength of the individual ingredients gave the surprising results of inhibiting growth of salmonella pullorum.

EXAMPLES 12–103

In each of the following examples, Example 11 was repeated and the effectiveness of the material being substituted was tested according to the procedure of Example 5. The substituted compound was tested at the same dilution as the compound it replaced both individually and in the combination of ingredients. In each example the substituted compound tested individually according to the method of Example 5 did not inhibit growth whereas the combination of the three ingredients including the substituted compound did inhibit growth even though they were used at one-half strength.

EXAMPLE 12

EXAMPLE 11 was repeated with benzethonium chloride substituted for the benzalkonium chloride. The material was tested according to the procedure of Example 5 and inhibited growth of the salmonella pullorum. This inhibition of growth can only be explained by the combination of the 3 ingredients acting synergistically together.

EXAMPLE 13

The test of Example 11 was repeated with cetyl-trimethyl ammonium bromide substituted for the benzalkonium chloride. The combination when tested according to the method of Example 5 acted synergistically in that it inhibited growth of the salmonella pullorum.

EXAMPLE 14

Example 11 was repeated with myristyl trimethyl ammonium bromide used in place of the benzalkonium chloride. The combination of the 3 ingredients acted synergistically to inhibit growth of the bacteria when tested according to the method of Example 5.

EXAMPLE 15

Example 11 was repeated with 6-tertiary-butyl-meta-cresol substitued for the 2-isopropyl-5-methyl-phenol. The combination of the 3 ingredients when tested according to the procedure of Example 5 acted synergistically to inhibit growth of the bacteria.

EXAMPLE 16

Example 11 was repeated with para-tertiary-amyl-phenol substituted for the 2-isopropyl-5-methyl-phenol. The combination of ingredients was tested as a disinfectant composition according to the procedure of Example 5 and acted synergistically to inhibit growth of the salmonella pullorum.

EXAMPLE 17

Example 11 was repeated with ortho-cresol used in place of the 2-isopropyl-5-methyl-phenol. The combination of ingredients when tested according to the method of Example 5 inhibited growth of the salmonella pullorum and this can only be explained on the basis that the 3 ingredients acted synergistically together.

EXAMPLE 18

Example 11 was repeated with para-cresol being substituted for the 2-isopropyl-5-methyl-phenol. When tested according to the method of Example 5 the combination of ingredients inhibited growth of the bacteria and this inhibition of growth is due to the 3 ingredients acting synergistically in combination.

EXAMPLE 19

Example 11 was repeated with 2-bromo-4-tert butylphenol substituted for the 2-isopropyl-5-methyl-phenol. The material was tested according to the procedure of Example 5 and inhibited growth of the salmonella pullorum. This inhibition of growth can only be explained by the combination of the 3 ingredients acting synergistically together.

EXAMPLE 20

The test of Example 11 was repeated with m-bromophenol substituted for the 2-isopropyl-5-methyl-phenol. The combination when tested according to the method of Example 5 acted synergistically in that it inhibited growth of the salmonella pullorum.

EXAMPLE 21

Example 11 was repeated with p-bromophenol used in place of the 2-isopropyl-5-methyl-phenol. The combination of the 3 ingredients acted synergistically to inhibit growth of the bacteria when tested according to the method of Example 5.

EXAMPLE 22

Example 11 was repeated with o-bromophenol substituted for the 2-isopropyl-5-methyl-phenol. The combination of the 3 ingredients when tested according to the procedure of Example 5 acted synergistically to inhibit growth of the bacteria.

EXAMPLE 23

Example 11 was repeated with 6-tert-butyl-m-cresol substituted for the 2-isopropyl-5-methyl-phenol. The combination of ingredients was tested as a disinfectant composition according to the procedure of Example 5 and acted synergistically to inhibit growth of the salmonella pullorum

EXAMPLE 24

Example 11 was repeated with o-tert-butylphenol used in place of the 2-isopropyl-5-methyl-phenol. The combination of ingredients when tested according to the method of Example 5 inhibited growth of the salmonella pullorum and this can only be explained on the basis that the 3 ingredients acted synergistically together.

EXAMPLE 25

Example 11 was repeated with p-sec-butylphenol being substituted for the 2-isopropyl-5-methyl-phenol. When tested according to the method of Example 5 the combination of ingredients inhibited growth of the bacteria and this inhibition of growth is due to the 3 ingredients acting synergistically in combination.

EXAMPLE 26

Example 11 was repeated with p-tert-butylphenol substituted for the 2-isopropyl-5-methyl-phenol. The material was tested according to the procedure of Example 5 and inhibited growth of the salmonella pullorum. This inhibition of growth can only be explained by the combination of the 3 ingredients acting synergistically together.

EXAMPLE 27

The test of Example 11 was repeated with 4-chloro-3-methylphenol substituted for the 2-isopropyl-5-methyl-phenol. The combination when tested according to the method of Example 5 acted synergistically in that it inhibited growth of the salmonella pullorum.

EXAMPLE 28

Example 11 was repeated with 4-chloro-2-methyl-phenol used in place of the 2-isopropyl-5-methyl-phenol. The combination of the 3 ingredients acted synergistically to inhibit growth of the bacteria when tested according to the method of Example 5.

EXAMPLE 29

Example 11 was repeated with m-chlorophenol substituted for the 2-isopropyl-5-methyl-phenol. The combination of the 3 ingredients when tested according to the procedure of Example 5 acted synergistically to inhibit growth of the bacteria.

EXAMPLE 30

Example 11 was repeated with 0-chlorophenol substituted for the 2-isopropyl-5-methyl-phenol. The combination of ingredients was tested as disinfectant composition according to the procedure of Example 5 and acted synergistically to inhibit growth of the salmonella pullorum.

EXAMPLE 31

Example 11 was repeated with p-chlorophenol used in place of the 2-isopropyl-5-methyl-phenol. The combination of ingredients when tested according to the method of Example 5 inhibited growth of the salmonella pullorum and this can only be explained on the basis that the 3 ingredients acted synergistically together.

EXAMPLE 32

Example 11 was repeated with m-cresol being substituted for the 2-isopropyl-5-methyl-phenol. When tested according to the method of Example 5 the combination of ingredients inhibited growth of the bacteria and this inhibition of growth is due to the 3 ingredients acting synergistically in combination.

EXAMPLE 33

Example 11 was repeated with 4,6-dibromo-o-cresol substituted for the 2-isopropyl-5-methyl-phenol. The material was tested according to the procedure of Example 5 and inhibited growth of the salmonella pullorum. This inhibition of growth can only be explained by the combination of the 3 ingredients acting synergistically together.

EXAMPLE 34

The test of Example 11 was repeated with 2,6-dibromo-p-cresol substituted for the 2-isopropyl-5-methyl-phenol. The combination when tested according to the method of Example 5 acted synergistically in that it inhibited growth of the salmonella pullorum.

EXAMPLE 35

Example 11 was repeated with 2,4-dibromophenol used in place of the 2-isopropyl-5L -methyl-phenol. The combination of the 3 ingredients acted synergistically to inhibit growth of the bacteria when tested according to the method of Example 5.

EXAMPLE 36

Example 11 was repeated with 2,6-dibromophenol substituted for the 2-isopropyl-5-mehtyl-phenol. The combination of the 3 ingredients when tested according to the procedure of Example 5 acted synergistically to inhibit growth of the bacteria.

EXAMPLE 37

Example 11 was repeated with 2,4-dichlorophenol substituted for the 2-isopropyl-5-methyl-phenol. The combination of ingredients was tested as a disinfectant composition according to the procedure of Example 5 and acted synergistically to inhibit growth of the salmonella pullorum.

EXAMPLE 38

Example 11 was repeated with 2,5-dichlorophenol used in place of the 2-isopropyl-5-methyl-phenol. The combination of ingredients when tested according to the method of Example 5 inhibited growth of the salmonella pullorum and this can only be explained on the basis that the 3 ingredients acted synergistically together.

EXAMPLE 39

Example 11 was repeated with 2-4-dimethylphenol being substituted for the 2-isopropyl-5-methyl-phenol. When tested according to the method of Example 5 the combination of ingredients inhibited growth of the bacteria and this inhibition of growth is due to the 3 ingredients acting synergistically in combination.

EXAMPLE 40

Example 11 was repeated with 2,5-dimethylphenol substituted for the 2-isopropyl-5-methyl-phenol. The material was tested according to the procedure of Example 5 and inhibited growth of the salmonella pullorum. This inhibition of growth can only be explained by the combination of the 3 ingredients acting synergistically together.

EXAMPLE 41

The test of Example 11 was repeated with 2,6-dimethylphenol substituted for the 2-isopropyl-5-methyl-phenol. The combination when tested according to the method of Example 5 acted synergistically in that it inhibited growth of the salmonella pullorum.

EXAMPLE 42

Example 11 was repeated with 3,4-dimethylphenol used in place of the 2-isopropyl-5-methyl-phenol. The combination of the 3 ingredients acted synergistically to inhibit growth of the bacteria when tested according to the method of Example 5.

EXAMPLE 43

Example 11 was repeated with 3,5-dimethylphenol substituted for the 2-isopropyl-5-methyl-phenol. The combination of the 3 ingredients when tested according to the procedure of Example 5 acted synergistically to inhibit growth of the bacteria.

EXAMPLE 44

Example 11 was repeated with 2,4-di-tert-pentylphenol substituted for the 2-isopropyl-5-methyl-phenol. The combination of ingredients was tested as a disinfectant composition according to the procedure of Example 5 and acted synergistically to inhibit growth of the salmonella pullorum.

EXAMPLE 45

Example 11 was repeated with 2,6-di-iso-propylphenol used in place of the 2-isopropyl-5-methyl-phenol. The combination of ingredients when tested according to the method of Example 5 inhibited growth of the salmonella pullorum and this can only be explained on the basis that the 3 ingredients acted synergistically together.

EXAMPLE 46

Example 11 was repeated with o-ethylphenol being substituted for the 2-isopropyl-5-methyl-phenol. When tested according to the method of Example 5 the combination of ingredients inhibited growth of the bacteria and this inhibition of growth is due to the 3 ingredients acting synergistically in combination.

EXAMPLE 47

Example 11 was repeated with p-ethylphenol substituted for the 2-isopropyl-5-methyl-phenol. The material was tested according to the procedure of Example 5 and inhibited growth of the salmonella pullorum. This inhibition of growth can only be explained by the combination of the 3 ingredients acting synergistically together.

EXAMPLE 48

The test of Example 11 was repeated with p-fluorophenol substituted for the 2-isopropyl-5-methyl-phenol. The combination when tested according to the method of Example 5 acted synergistically in that it inhibited growth of the salmonella pullorum.

EXAMPLE 49

Example 11 was repeated with m-iodophenol used in place of the 2-isopropyl-5-methyl-phenol. The combination of the 3 ingredients acted synergistically to inhibit growth of the bacteria when tested according to the method of Example 5.

EXAMPLE 50

Example 11 was repeated with o-iodophenol substituted for the 2-isopropyl-5-methyl-phenol. The combination of the 3 ingredients when tested according to the procedure of Example 5 acted synergistically to inhibit growth of the bacteria.

EXAMPLE 51

Example 11 was repeated with p-iodophenol substituted for the 2-isopropyl-5-methyl-phenol. The combination of ingredients was tested as a disinfectant composition according to the procedure of Example 5 and acted synergistically to inhibit growth of the salmonella pullorum.

EXAMPLE 52

Example 11 was repeated with p-pentylphenol used in place of the 2-isopropyl-5-methyl-phenol. The combination of ingredients when tested according to the method of Example 5 inhibited growth of the salmonella pullorum and this can only be explained on the basis that the 3 ingredients acted synergistically together.

EXAMPLE 53

Example 11 was repeated with p-tert-pentylphenol being substituted for the 2-isopropyl-5-methyl-phenol. When tested according to the method of Example 5 the combination of ingredients inhibited growth of the bacteria and this inhibition of growth is due to the 3 ingredients acting synergistically in combination.

EXAMPLE 54

Example 11 was repeated with phenol substituted for the 2-isopropyl-5-methyl-phenol. The material was tested according to the procedure of Example 5 and inhibited growth of the salmonella pullorum. This inhibition of growth can only be explained by the combination of the 3 ingredients acting synergistically together.

EXAMPLE 55

Example 11 was repeated with methyl dodecylbenzyl trimethyl ammonium chloride substituted for the benzalkonium chloride. The material was tested according to the procedure of Example 5 and inhibited growth of the salmonella pullorum. This inhibition of growth can only be explained by the combination of the 3 ingredients acting synergistically together.

EXAMPLE 56

The test of Example 11 was repeated with methyl dodecylxylylene bis (trimethyl ammonium chloride) substituted for the benzalkonium chloride. The combinaion when tested according to the method of Example 5 acted synergistically in that it inhibited growth of the salmonella pullorum.

EXAMPLE 57

Example 11 was repeated with methyl dodecylbenzyl trimethyl ammonium chloride and methyl dodecylxylylene bis (trimethyl ammonium chloride) substituted for the benzalkonium chloride. The combination of the 3 ingredients when tested according to the procedure of Example 5 acted synergistically to inhibit growth of the bacteria.

EXAMPLE 58

Example 11 was repeated with hexyl benzyltrimethyl ammonium bromide substituted for the benzalkonium chloride. The combination of ingredients was tested as a disinfectant composition according to the procedure of Example 5 and acted synergistically to inhibit growth of the salmonella pullorum.

EXAMPLE 59

Example 11 was repeated with ethyl decyl benzyltrimethyl ammonium chloride used in place of the benzalkonium chloride. The combination of ingredients when tested according to the method of Example 5 inhibited growth of the salmonella pullorum and this can only be explained on the basis that the 3 ingredients acted synergistically together.

EXAMPLE 60

Example 11 was repeated with octyl benzyltrimethyl ammonium chloride being substituted for the benzalkonium chloride. When tested according to the method of Example 5 the combination of ingredients inhibited growth of the bacteria and this inhibited of growth is due to the 3 ingredients acting synergistically in combination.

EXAMPLE 61

Example 11 was repeated with methyl benzyltrimethyl ammonium iodide substituted for the benzalkonium chloride. The material was tested according to the procedure of Example 5 and inhibited growth of the salmonella pullorum. This inhibition of growth can only be explained by the combination of the 3 ingredients acting synergistically together.

EXAMPLE 62

The test of Example 11 was repeated with butyl xylylene bis (trimethyl ammonium chloride). The combination when tested according to the method of Example 5 acted synergistically in that it inhibited growth of the salmonella pullorum.

EXAMPLE 63

Example 11 was repeated with diethyl xylylene bis (trimethyl ammonium chloride) used in place of the benzalkonium chloride. The combination of the 3 ingredients acted synergistically to inhibit growth of the bacteria when tested according to the method of Example 5.

EXAMPLE 64

Example 11 was repeated with propyl octyl xylylene bis (trimethyl ammonium chloride) substituted for the benzalkonium chloride. The combination of the 3 ingredients when tested according to the procedure of Example 5 acted synergistically to inhibit growth of the bacteria.

EXAMPLE 65

Example 11 was repeated with benzyldimethylphenylammonium chloride substituted for the benzalkonium chloride. The material was tested according to the procedure of Example 5 and inhibited growth of the salmonella pullorum. This inhibition of growth can only be explained by the combination of the 3 ingredients acting synergistically together.

EXAMPLE 66

The test of Example 11 was repeated with benzyldimethyl{2-[2-(m-methyl-p-1,1,3,3-tetramethylbutylphenoxy) ethoxy] ethyl} ammonium chloride monohydrate substituted for the benzalkonium chloride. The combination when tested according to the method of Example 5 acted synergistically in that it inhibited growth of the salmonella pullorum.

EXAMPLE 67

Example 11 was repeated with hexadecyltrimethylammonium chloride used in place of the benzalkonium chloride. The combination of the 3 ingredients acted synergistically to inhibit growth of the bacteria when tested according to the method of Example 5.

EXAMPLE 68

Example 11 was repeated with octadecyltrimethylammonium chloride substituted for the benzalkonium chloride. The material was tested according to the procedure of Example 5 and inhibited growth of the salmonella pullorum. This inhibition of growth can only be explained by the combination of the 3 ingredients acting synergistically together.

EXAMPLE 69

The test of Example 11 was repeated with (2-acetoxypropyl) trimethylammonium chloride substituted for the benzalkonium chloride. The combination when tested according to the method of Example 5 acted synergistically in that it inhibited growth of the salmonella pullorum.

EXAMPLE 70

Example 11 was repeated with (2-carbamoyloxyethyl) trimethylammonium chloride used in place of the benzalkonium chloride. The combination of the 3 ingredients acted synertistically to inhibit growth of the bacteria when tested according to the method of Example 5.

EXAMPLE 71

Example 11 was repeated with 1-benzyl-3-(dimethylcarbamoyloxy) pyridinium bromide substituted for the benzalkonium chloride. The material was tested according to the procedure of Example 5 and inhibited growth of the salmonella pullorum. This inhibition of growth can only be explained by the combination of the 3 ingredients acting synergistically together.

EXAMPLE 72

The test of Example 11 was repeated with furfuryltrimethylammonium iodide substituted for the benzalkonium chloride. The combination when tested according to the method of Example 5 acted synergistically in that it inhibited growth of the salmonella pullorum.

EXAMPLE 73

Example 11 was repeated with [m-(dimethylcarbamoyloxy)-phenyl]trimethylammonium bromide used in place of the benzalkonium chloride. The combination of the 3 ingredients acted synergistically to inhibit growth of the bacteria when tested according to the method of Example 5.

EXAMPLE 74

Example 11 was repeated with p-(benzyloxy) phenol substituted for the 2-isopropyl-5-methyl-phenol. When tested according to the method of Example 5 the combination of ingredients inhibited growth of the bacteria and this inhibition of growth is due to the 3 ingredients acting synergistically in combination.

EXAMPLE 75

Example 11 was repeated with 4-bromo-2,6-dimethylphenol substituted for the 2-isopropyl-5-methylphenol. The material was tested according to the procedure of Example 5 and inhibited growth of the salmonella pullorum. This inhibition of growth can only be explained by the combination of the 3 ingredients acting synergistically together.

EXAMPLE 76

The test of Example 11 was repeated with α bromo-5-nitro-o-cresol substituted for the 2-isopropyl-5-methylphenol. The combination when tested according to the method of Example 5 acted synergistically in that it inhibited growth of the salmonella pullorum.

EXAMPLE 77

Example 11 was repeated with p-n-butoxyphenol used in place of the 2-isopropyl-5-methyl-phenol. The combination of the 3 ingredients acted synergistically to inhibit growth of the bacteria when tested according to the method of Example 5.

EXAMPLE 78

Example 11 was repeated with 4-chloro-3,5-dimethylphenol substituted for the 2-isopropyl-5-methylphenol. The combination of the 3 ingredients when tested according to the procedure of Example 5 acted synergistically co inhibit growth of the bacteria.

EXAMPLE 79

Example 11 was repeated with 2-chloro-4-phenylphenol substituted for the 2-isopropyl-5-methylphenol. The combination of ingredients was tested as a disinfectant composition according to the procedure of Example 5 and acted synergistically to inhibit growth of the salmonella pullorum.

EXAMPLE 80

Example 11 was repeated with 2,6-di-tert-butyl-p-cresol used in place of the 2-isopropyl-5-methylphenol. The combination of ingredients when tested according to the method of Example 5 inhibited growth of the salmonella pullorum and this can only be explained on the basis that the 3 ingredients acted synergistically together.

EXAMPLE 81

Example 11 was repeated with 2,6-di-tert-butylphenol being substituted for the 2-isopropyl-5-methylphenol. When tested according to the method of Example 5 the combination of ingredients inhibited growth of the bacteria and this inhibition of growth is due to the 3 ingredients acting synergistically in combination.

EXAMPLE 82

Example 11 was repeated wtih m-ethoxyphenol substituted for the 2-isopropyl-5-methyl-phenol. The material was tested according to the procedure of Example 5 and inhibited growth of the salmonella pullorum. This inhibition of growth can only be explained by the combination of the 3 ingredients acting synergistically together.

EXAMPLE 83

The test of Example 11 was repeated with o-ethoxyphenol substituted for the 2-isopropyl-5-methylphenol. The combination when tested according to the method of Example 5 acted synergistically in that it inhibited growth of the salmonella pullorum.

EXAMPLE 84

Example 11 was repeated wih p-ethoxyphenol used in place of the 2-isopropyl-5-methyl-phenol. The combination of the 3 ingredients acted synergistically to inhibit growth of the bacteria when tested according to the method of Example 5.

EXAMPLE 85

Example 11 was repeated with 2-methoxy-4-methylphenol substituted for the 2-isopropyl-5-methylphenol. The combination of the 3 ingredients when tested according to the procedure of Example 5 acted synergistically to inhibit growth of the bacteria.

EXAMPLE 86

Example 11 was repeated with m-methoxyphenol substituted for the 2-isopropyl-5-methyl-phenol. The combination of ingredients was tested as a disinfectant composition according to the procedure of Example 5 and acted synergistically to inhibit growth of the salmonella pullorum.

EXAMPLE 87

Example 11 was repeated with p-methoxyphenol used in place of the 2-isopropyl-5-methyl-phenol. The combination of ingredients when tested according to the method of Example 5 inhibited growth of the salmonella pullorum and this can only be explained on the basis that the 3 ingredients acted synergistically together.

EXAMPLE 88

Example 11 was repeated with 2-bromo-4-phenylphenol being substituted for the 2-isopropyl-5-methyl-phenol. When tested according to the method of Example 5 the combination of ingredients inhibited growth of the bacteria and this inhibition of growth is due to the 3 ingredients acting synergistically in combination.

EXAMPLE 89

Example 11 was repeated with 2-chloro-4-nitrophenol substituted for the 2-isopropyl-5-methyl-phenol. The material was tested according to the procedure of Example 5 and inhibited growth of the salmonella pullorum. This inhibition of growth can only be explained by the combination of the 3 ingredients acting synergistically together.

EXAMPLE 90

The test of Example 11 was repeated with 2-chloro4,6-dinitrophenol substituted for the 2-isopropyl-5-methyl phenol. The combination when tested according to the method of Example 5 acted synergistically in that it inhibited growth of the salmonella pullorum.

EXAMPLE 91

Example 11 was repeated with 2,6-dichloro-4-nitrophenol used in place of the 2-isopropyl-5-methyl-phenol. The combination of the 3 ingredients acted synergistically to inhibit growth of the bacteria when tested according to the method of Example 5.

EXAMPLE 92

Example 11 was repeated with 2,6-dibromo-4-nitrophenol substituted for the 2-isopropyl-5-methyl-phenol. The combination of the 3 ingredients when tested according to the procedure of Example 5 acted synergistically to inhibit growth of the bacteria.

EXAMPLE 93

Example 11 was repeated with 4,6-dinitro-o-cresol substitute for the 2-isopropyl-5-methyl-phenol. The combination of ingredients was tested as a disinfectant composition according to the procedure of Example 5 and acted synergistically to inhibit growth of the salmonella pullorum.

EXAMPLE 94

Example 11 was repeated with 2,4-dinitrophenol used in place of the 2-isopropyl-5-methyl-phenol. The combination of ingredients when tested according to the method of Example 5 inhibited growth of the salmonella pullorum and this can only be explained on the basis that the 3 ingredients acted synergistically together.

EXAMPLE 95

Example 11 was repeated with 2-amino-4-chlorophenol being substituted for the 2-isopropyl-5-methyl-phenol. When tested according to the method of Example 5 the combination of ingredients inhibited growth of the bacteria and this inhibition of growth is due to the 3 ingredients acting synergistically in combination.

EXAMPLE 96

Example 11 was repeated with 4-amino-2,6-dichlorophenol substituted for the 2-isopropyl-5-methyl-phenol. The material was tested according to the procedure of Example 5 and inhibited growth of the salmonella pullorum. This inhibition of growth can only be explained by the combination of the 3 ingredients acting synergistically together.

EXAMPLE 97

The test of Example 11 was repeated with 2-amino-4-nitrophenol substituted for the 2-isopropyl-5-methyl-phenol. The combination when tested according to the method of Example 5 acted synergistically in that it inhibited growth of the salmonella pullorum.

EXAMPLE 98

Example 11 was repeated with o-aminophenol used in place of the 2-isopropyl-5-methyl-phenol. The combination of the 3 ingredients acted synergistically to inhibit growth of the bacteria when tested according to the method of Example 5.

EXAMPLE 99

Example 11 was repeated with 2-amino-4-phenylphenol substituted for the 2-isopropyl-5-methyl-phenol. The combination of the 3 ingredients when tested according to the procedure of Example 5 acted synergistically to inhibit growth of the bacteria.

EXAMPLE 100

Example 11 was repeated with p-benzylaminophenol substituted for the 2-isopropyl-5-methyl-phenol. The combination of ingredients was tested as a disinfectant composition according to the procedure of Example 5 and acted synergistically to inhibit growth of the salmonella pullorum.

EXAMPLE 101

Example 11 was repeated with 2,6-dibromo-4-aminophenol used in place of the 2-isopropyl-5-methyl-phenol. The combination of ingredients when tested according to the method of Example 5 inhibited growth of the salmonella pullorum and this can only be explained on the basis that the 3 ingredients acted synergistically together.

EXAMPLE 102

Example 11 was repeated with m-diethylaminophenol being substituted for the 2-isopropyl-5-methylphenol. When tested according to the method of Example 5 the combination of ingredients inhibited growth of the bacteria and this inhibition of growth is due to the 3 ingredients acting synergistically in combination.

EXAMPLE 103

Example 11 was repeated with m-dimethylaminophenol substituted for the 2-isopropyl-5-methylphenol. The material was tested according to the procedure of Example 5 and inhibited growth of the salmonella pullorum. This inhibition of growth can only be explained by the combination of the 3 ingredients acting synergistically together.

It will be understood that the claims are intended to cover all changes and modifications of the preferred embodiments of the invention, herein chosen for the purpose of illustration, which do not constitute departures from the spirit and scope of the invention.

What is claimed is:

1. A disinfectant composition comprising an admixture of
    a. from about 10 to about 150 parts formaldehyde;
    b. from about 1 to about 20 parts of a methyldodecylbenzyl trimethyl ammonium halogen salt wherein the halogen is selected from the group consisting of chlorine, bromine, and iodine; and
    c. from about 1 to about 20 parts of 5 methyl-2-isopropyl-1-phenol.

2. The disinfectant composition of claim 1 further comprising methyldodecylxylylene bis (tri-methyl ammonium chloride).

3. A disinfectant composition comprising an admixture of:
    a. from about 10 to about 150 parts formaldehyde;
    b. from about 1 to about 20 parts benzalkonium chloride; and
    c. from about 1 to about 20 parts 2-isopropyl-5-methyl-phenol.

4. A disinfectant composition comprising an admixture of:
    a. from about 20 to about 150 parts formaldehyde;
    b. from about 1 to about 20 parts benzethonium chloride; and
    c. from about 1 to about 20 parts para-cresol.

* * * * *